(12) United States Patent
Daly et al.

(10) Patent No.: US 6,306,835 B1
(45) Date of Patent: Oct. 23, 2001

(54) BIOCIDAL CHITOSAN DERIVATIVES

(75) Inventors: William H. Daly; Melissa A. Manuszak-Guerrini, both of Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/154,365

(22) Filed: Sep. 16, 1998

Related U.S. Application Data

(60) Provisional application No. 60/135,500, filed on Sep. 23, 1997.

(51) Int. Cl.[7] .................................................. A01N 43/04
(52) U.S. Cl. ........................ 514/55; 424/400; 424/401; 424/405; 424/406; 424/407; 424/409; 424/78.02; 424/78.07; 424/484; 424/486; 424/487
(58) Field of Search ..................... 424/400, 401, 424/405–407, 409, 484, 486, 489, 78.02, 78.03, 78.07; 514/55

(56) References Cited

U.S. PATENT DOCUMENTS

| | | | |
|---|---|---|---|
| 3,299,566 | 1/1967 | MacMullen | 47/1 |
| 4,772,689 | * 9/1988 | Lang et al. | 536/20 |
| 4,772,690 | * 9/1988 | Lang et al. | 536/20 |
| 5,696,098 | 12/1997 | Muraki | 514/55 |

FOREIGN PATENT DOCUMENTS

| | | |
|---|---|---|
| 3501891 | 7/1986 | (DE) . |
| 3502833 | 7/1986 | (DE) . |
| 3573277 | * 10/1986 | (DE) . |
| 0 105 106 | 4/1984 | (EP) . |
| 61151112 | 7/1986 | (JP) . |
| 61216648 | 9/1986 | (JP) . |
| 62138596 | 10/1987 | (JP) . |
| 61285258 | 12/1987 | (JP) . |
| 63014714 | 1/1988 | (JP) . |

OTHER PUBLICATIONS

Kim, C. et al., "Synthesis and Antibacterial Activity of Water–Soluble Chitin Derivatives," *Polymers for Advanced Technologies*, vol. 8, pp. 319–325 (1997).

Lang, G. et al., "Chitosan derivatives in cosmetics," *Chem. Abstr.* 105:139429b, German Patent 3,501,891 (1986).

Lang, G. et al., "Chitosan derivatives in cosmetics," *Chem. Abstr.* 105:139430v, German Patent 3,502,833 (1986).

Lang, G. et al., "Hydroxypropylation of Chitosan," pp. 389–395 in G. Skjak–Braek et al. (eds.), Chitin and Chitosan, Sources, Chemistry, Biochemistry, Physical Properties and Applications (1989).

Lang, G. et al., "Quaternary hydroxyalkyl chitosan cosmetic for hair and skin," *Chem. Abstr.* 106:38223v, German Patent 3,513,277 (1986).

Lang, G. et al., "The Use of Chitosan in Cosmetics," pp. 139–147 in G. Skjak–Braek et al. (eds.), Chitin and Chitosan, Sources, Chemistry, Biochemistry, Physical Properties and Applications (1989).

Macossayt, J., "Synthesis and Characterization of Water Soluble Chitosan Derivatives," Ph.D. Dissertation, Louisana State University, Baton Rouge, pp. 46–48, 110, and 113–114 (1995).

Macossay, J. et al., "Production of water soluble chitosan derivatives by treatment with substituted oxiranes," Abstract, 208th American Chemical Society National Meeting (CELL), Washington, DC (Aug. 1994).

Yalpani, M. et al., "Antimicrobial Activity of Some Chitosan Derivatives," pp. 543–547 in C. Brine et al. (Ed.), *Advances in Chitin and Chitosan* (1992).

* cited by examiner

Primary Examiner—Neil S. Levy
(74) Attorney, Agent, or Firm—John H. Runnels

(57) ABSTRACT

3-trimethylammonium-2-hydroxypropyl-N-chitosan (CHI-Q188) and related chitosan derivatives exhibit antimicrobial activity at concentrations as low as 10–20 $\mu$g/mL, an order of magnitude lower than the concentrations at which any previous chitosan derivative has been reported to exhibit antimicrobial activity. These compounds may be used as preservatives in cosmetic formulations, and as antimicrobial pharmaceutical agents.

6 Claims, No Drawings

BIOCIDAL CHITOSAN DERIVATIVES

The benefit of the Sep. 23, 1997 filing date of provisional application 60/135,500 (which was a conversion of nonprovisional application 08/935,880) is claimed under 35 U.S.C. §119(e).

This invention pertains to antimicrobial compounds and their methods of use, particularly to certain antimicrobial compounds derived from chitosan.

Preservation of a product is the retardation or prevention of its deterioration from the time of manufacture until the consumer completely uses all of the product in its container. Many components used in cosmetic products, such as fats, oils, and surfactants, are susceptible to degradation by microorganisms. A product may harbor a growing bacterial or flingal population without outward visible signs. A contaminated product may lose effectiveness and can cause infection, particularly if placed in contact with broken or damaged skin. Preservatives are commonly added to personal care products to inhibit the growth of bacteria or fungi, to increase shelf life, and to protect the consumer from infection. Preservatives typically inhibit or prevent microbial growth by depleting water or nutrient sources, or by disrupting cell membranes.

In many applications, it is highly desirable that the preservatives should not only protect the product until its packaging is first opened by the consumer, but also that the preservatives should prevent or reduce the growth of contaminating microorganisms introduced to the product when used by the consumer. A typical goal is that products with preservative agents should self-sterilize within 24 hours of contamination resulting from normal conditions of use. Products containing less than 15% alcohol, and having a pH range between about 3 and about 11, are particularly prone to microbial spoilage.

The most commonly used preservatives in cosmetic formulations are listed in Table 1. Methylparaben (Methyl-4-hydroxybenzoate) is the most frequently used cosmetic preservative. It is common to use mixtures of preservatives that are effective against different microorganisms, or that interact synergistically with one another. Quaternary ammonium compounds, or "quats," have been tested for irritation and sensitization properties; at concentrations below 0.1%, most quats appear to cause little or no irritation. However, most of the quats listed as preservatives have only been "monographed" by the United States Food and Drug Administration for use as conditioning agents in hair or skin products, because they are not sufficiently active to be considered primary antimicrobial additives.

TABLE 1

Commonly Used Preservatives in Cosmetics

| ACIDS | PARABENS |
|---|---|
| p-Hydroxybenzoic acid | Methyl p-hydroxybenzoate |
| Benzoic acid | Ethyl p-hydroxybenzoate |
| Sorbic acid | Propyl p-hydroxybenzoate |
| Dehydroacetic acid | Butyl p-hydroxybenzoate |
| Formic acid | Benzyl p-hydroxybenzoate |
| Salicylic acid | ANILIDES |
| Boric acid | Tetrachlorosalicylanilide |
| Vanillic acid | Trichlorocarbanilide |
| o,p-Chlorobenzoic acid | Trichlorsalicylanilide |
| Propionic acid | PHENOLS |
| Sulfurous acid | Phenol |
| Trichlorophenylacetic acid | Cresol |
| METAL-CONTAINING | Chlorothymol |
| Sodium ethyl mercurithiosalicylate | Methylchlorothymol |
|  | Chlorobutanol |
| Phenyl mercury acetate | o-Phenylphenol |
| Phenyl mercury borate | Parachlormetacresol |
| Phenyl mercury nitrate | Parachlormetaxylenol |
| QUATS | β-Phenoxyethylalcohol |
| Benzethonium chloride | Dichlorophene |
| Benzalkonium chloride | Hexachlorophene |
| Cetyltrimethyl ammonium bromide | Vanillin |
|  | Ethyl vanillin |
| Cetyl pyridinium chloride | 2-Bromo-2-nitro-1,3-propanediol |
| Tetramethylthiorandisulfide | β-Phenoxypropylalcohol |
| Imidazolidinyl urea | Monomethylol dimethyl hydantoin |
| Dimethyldidodeceyl ammonium chloride |  |

Chitin, poly β-(1→4)-2-acetamido-2-deoxy-D-glucopyranose, is a major constituent of arthropod exoskeletons. Chitin is the second most abundant biopolymer in nature. Chitin is extracted commercially from the exoskeletons or shells of crustaceans such as shrimp, crab, and crawfish by demineralizing crushed shells and extracting proteins and polypeptides. Chitosan, poly β-(1→4)-2-amino-2-deoxy-D-glucopyranose, is a natural biopolymer that may be obtained by alkaline deacetylation of chitin.

Among the characteristics of chitosan that may be varied as needed for a particular application are the degree of deacetylation (compared to chitin) and the molecular weight. The viscosity of solutions containing chitosan is affected by the degree of deacetylation, molecular weight, concentration, ionic strength, pH and temperature. Generally, increases in temperature cause decreases in the viscosity of the solution. The effect of pH on viscosity depends on the particular acid used. Native chitosan is soluble in organic acids when the pH is less than 6, and is insoluble in water, alkali, or organic solvents. However, water soluble salts of chitosan may be formed by neutralization with acids such as hydrochloric acid, acetic acid, lactic acid, or formic acid. Chitosan has been used in water treatment, paper manufacturing, agriculture, food processing, cosmetics, biotechnology, and medicine.

A quaternary nitrogen functional group is a part of many biologically active compounds. Some quaternary ammonium compounds exhibit antimicrobial activity. The antimicrobial action is believed to result when the compounds are adsorbed onto the bacterial cell surface, increasing the permeability of the lipid cell membrane, and causing death through the loss of essential cell materials.

Quaternary ammonium compounds have been used in water treatment, in liquid laundry detergents as sanitizers, in preoperative treatment of surgical patients, and in disinfection of surgical instruments. In the cosmetics and pharmaceutical industries, they have been used as preservatives in consumer products. They are used as disinfectants of food contact surfaces, and are incorporated into latex paints as fungistats.

Some quaternary ammonium polymers have been reported to have antimicrobial activity. These polymers have been used in areas including water treatment, health care and hygienic applications, coatings, textiles, disinfection of air and other gases, and as preservatives. Quaternary polymers are generally more active than their corresponding monomers particularly against gram-positive bacteria. This effect is believed to be due to adsorption of the polymers onto the bacterial cell surface and membrane, with subsequent disruption of membrane integrity. Antimicrobial activity generally increases as the content of the quaternary ammonium moiety increases.

The mechanism of action for quaternary polymers has not been extensively studied. It is probable that "polyquats" interact with bacteria in a similar manner as do the non-polymeric quats: adsorption onto the bacterial cell surface, diffusion through the cell wall, and binding to the cytoplasmic membrane. Adsorption onto the bacterial surface interferes with permeability and transport across the cell membrane. This interference disrupts the cytoplasmic membrane and causes leakage of potassium ions and other low molecular weight cytoplasmic components. Leakage of macrocomponents of the cell and precipitation of cell components occur, and the microorganism dies.

Some quaternary ammonium polymers such as polyquaternium 18 and polyquaternium 27, previously used in cosmetic formulations as conditioners and thickeners, may exhibit some bacteriostatic properties. However, they have only been monographed by the United States Food and Drug Administration for use as conditioning agents in hair and skin care products, because they are not sufficiently active to be considered primary antimicrobial additives. A separate antimicrobial agent has typically been added to such products to achieve good storage stability. Quaternary ammonium polymers have previously been considered bacteriostatic, not bactericidal, because they require long contact times to actually kill microorganisms, and generally do not have broad spectrum activity.

G. Lang et al., "Quaternary hydroxyalkyl chitosan cosmetic for hair and skin," *Cliem. Abstr.* 106:38223v, German Patent 3,513,277 (1986) (English translation of abstract provided) discloses certain quaternary ammonium chitosan derivatives said to have better compatibility with surfactants and better solubility as compared to chitosan when used in hair and skin preparations.

G. Lang et al., "Chitosan derivatives in cosmetics," *Chem. Abstr.* 105:139429b, German Patent 3,501,891 (1986) (English translation of abstract provided); and G. Lang et al., "Chitosan derivatives in cosmetics," *Chem. Abstr.* 105:139430v, German Patent 3,502,833 (1986) (English translation of abstract provided) disclose certain quaternary ammonium chitosan derivatives said to be useful as ingredients in hair and skin cosmetics and preparations.

Lion Corp., Japanese patent 61-216648 (1986) (English translation of abstract provided) discloses the use of party deacetylated chitin in foods and drinks containing sucrose to prevent tooth decay and foul breath.

Lion Corp., Japanese patent 61-060701 (1986) (English translation of abstract provided) discloses the reaction of chitosan with certain quaternary ammonium salts; the process may involve further reaction with hydroxyalkylating agents. The resulting compounds were said to be water soluble, to have high cationic activity, to have film-forming properties, and to be useful as a cosmetic base material, flocculent, or antistatic agent.

Lion Corp., Japanese patent 61-285258 (1987) (English translation of abstract provided) discloses the preparation of certain quaternary ammonium chitosan derivatives, and certain uses for those derivatives, including uses as an adsorbent or a coating agent.

Lion Corp., Japanese patent 62-138596 (1987) (English translation of abstract provided) discloses a solid soap composition prepared by blending water-insoluble chitin and water-soluble chitin or chitosan or certain derivatives.

Lion Corp., Japanese patent 61-151112 (1986) (English translation of abstract provided) discloses certain water soluble chitin and chitosan derivatives, and their use in anti-caries preparations.

Lion Corp., Japanese patent 63-014714 (1988) (English translation of abstract provided) discloses compositions including certain water-soluble chitin and chitosan derivatives, and their use in cleaning and pasteurizing artificial teeth by desorbing *C. albicans*, and preventing *C. albicans* adhering to the teeth.

C. Kim et al., "Synthesis and Antibacterial Activity of Water-Soluble Chitin Derivatives," *Polymers for Advanced Technologies*, vol. 8, pp. 319–325 (1997) reported certain antibacterial activities of diethylaminoethyl-chitin, diethylaminoethyl-chitosan, and triethylaminoethyl-chitin. The triethylaminoethyl-chitin was the most active agent; it had a greater activity against *S. aureus* than *E. coli*. A concentration of 500 ppm was needed to kill all *S. aureus* within 120 minutes. Different molecular weight hydrolysates of diethylaminoethyl-chitin were examined; it was reported that antibacterial activity was dependent on molecular weight of the hydrolysate.

M. Yalpani et al., "Antimicrobial Activity of Some Chitosan Derivatives," pp. 543–547 in C. Brine et al. (Ed.), *Advances in Chitin and Chitosan* (1992) reports that the carbohydrate-branched derivatives 1-deoxy-1-glucit-1-yl chitosan and 1-deoxy-l-lactit-1-yl chitosan had activity against *Bacillus circulans*, but not *E. coli*, while chito-oligosaccharides of varying d.p.'s had activity against *E. coli*, but not against *B. circulans*.

There is an unfilled need for new antimicrobial agents suitable for use as preservatives in personal care products. There is also an unfilled need for new antimicrobial pharmaceuticals to which bacterial strains have not yet developed resistance.

It has been unexpectedly discovered that 3-trimethylammonium-2-hydroxypropyl-N-chitosan (CHI-Q188) and related chitosan derivatives exhibit antimicrobial activity at concentrations as low as 10–20 µg/mL, an order of magnitude lower than the concentrations at which any previous chitosan derivative has been reported to exhibit antimicrobial activity.

The class of compounds exhibiting this novel antimicrobial activity may be depicted generically as:

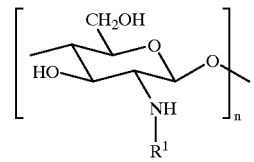

wherein $R^1$ denotes —H, —COCH$_3$, or —CH$_2$—CHOH—CH$_2$—N$^+$(CH$_3$)$_2$R$^2$X$^-$, in selected proportions corresponding to the desired degree of substitution; i.e., within a single polymeric or oligomeric molecule, some of the $R^1$s will be —H, some will be —CH$_2$—CHOH—CH$_2$—N$^+$(CH$_3$)$_2$R$^2$X$^-$, and (optionally) some may be —COCH$_3$; wherein the degree of substitution, the proportion of —CH$_2$—CHOH—CH$_2$—N$^+$(CH$_3$)$_2$R$^2$X$^-$ moieties, may be between about 10% and 100%; wherein $R^2$ denotes a substituted or unsubstituted alkyl or aryl group from $C_1$ to $C_{12}$; wherein X$^-$ denotes an anion such as chloride, bromide, iodide, hydrogen sulphate, acetate, lactate, formate, glutamate, etc.; and wherein "n" denotes the desired degree of polymerization, preferably 5 or greater. Without wishing to be bound by this theory, it is believed that the hydroxy group beta to the nitrogens is largely responsible for the increased antimicrobial activity of CHI-Q188 and related compounds in comparison to other chitosan derivatives.

These chitosan derivatives may be included in formulations where it is desirable to minimize bacterial attack. For example, they may be incorporated at low concentrations into cosmetic formulations, such as hair and skin formulations. These water-soluble derivatives may be used as thickeners, film formers, fixatives, emulsifiers, and additives to hair or skin formulations. They may also be used as biocides in medical applications such as surgical dressings, wound packing materials, and topical or injected drug formulations. They may also be used in water treatment, and in textile coating to reduce odor formation. Other applications include uses in household products, waste water treatment, antituberculin agents, and agricultural coatings.

TEST ORGANISMS AND EXPERIMENTAL TECHNIQUES

The strains of bacteria used in this study were received directly from the American Type Culture Collection (ATCC): *Escherichia coli* 25922, *Staphylococcus aureus* 29213, and *Pseudomonas aeruginosa* 27853. The cultures were stored frozen in a solution of nutrient broth and glycerol until used. The cells were maintained by growth of a culture overnight in 5 mL of nutrient broth. The next morning, 1 mL of the culture was resuspended in 25 mL of nutrient broth at room temperature and placed in a shaker-incubator for 4 hours at 150 rpm and 37° C. to obtain a cell density of at least $10^8$ cells/mL in mid-logarithmic growth phase. The optical density (OD) of the cell solution was measured at 600 nm with a spectrophotometer. When necessary, the suspensions were diluted with nutrient broth until the OD read 0.20±0.01 for *E. coli* or *P. aeruginosa*, and 0.40±0.01 for *S. aureus*. (These OD readings correspond to concentrations of about $10^8$ bacterial cells/mL of nutrient broth.) Aerobic plate counts (APCs) were used to confirm the population of each inoculum.

Nutrient broth was prepared by dissolving 8 g of soytrypsin digest protein per liter of deionized water. The pH of the solution was adjusted to 7.2±0.2 with 1 M sodium hydroxide. The nutrient broth was autoclaved prior to use.

Agar was prepared by dissolving 40 g of tryptic soy agar per liter of deionized water. The pH of the solution was adjusted to 7.2±0.2 with 1 M sodium hydroxide. The agar was autoclaved prior to use. Agar plates were prepared by pouring the hot, autoclaved agar into gamma-irradiated petri dishes. The dry agar plates were stored in a refrigerator prior to use.

3-trimethylammonium-2-hydroxypropyl-N-chitosan (CHI-Q188), a water-soluble, quaternary ammonium derivative of chitosan, was prepared by the method of J. Macossay et al., "Production of water soluble chitosan derivatives by treatment with substituted oxiranes," Abstract, 208th American Chemical Society National Meeting (CELL), Washington, DC (August 1994); and J. Macossay, "Synthesis and Characterization of Water Soluble Chitosan Derivatives," Ph.D. Dissertation, Louisiana State University, Baton Rouge, pp. 46–48, 110, and 113–114 (1995). Briefly, fresh regenerated chitosan was mixed with Quat 188 (Dow Chemical Co.) and NaOH. The mixture reacted at room temperature for 24 hours, at which time water was added and the temperature was increased to 50° C. for 24 hours. The reaction was then cooled to room temperature and neutralized with acetic acid, followed by dialysis and lyophilization to yield CHI-Q188. Alternatively, chitosan (or a chitosan derivative containing residual amino groups) may be treated with N-(3-chloro-2-hydroxypropyl) trimethyl ammonium chloride to yield the quaternized CHI-Q188 derivative. Alternatively, chitosan may be treated with an excess of epichlorohydrin, followed by treatment either with dimethylamine and iodomethane or with trimethyl amine, in either case in the presence of a catalytic amount of iodine, to obtain quaternary ammonium salts.

CHI-Q188 is depicted below, in which $X^-$ is an water-soluble anion such as chloride, bromide, iodide, hydrogen sulphate, acetate, lactate, formate, glutamate, pyruvate, ascorbate, alkylcarboxylates containing 2 to 20 carbon atoms, etc., and in which "n" represents the degree of polymerization:

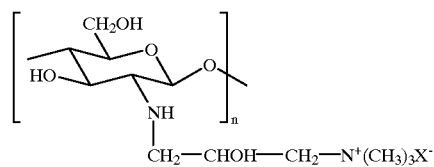

Aqueous solutions of 0.2% (w/v) methyl-4-hydroxybenzoate (methylparaben); 0.2% (w/v) 3-trimethylammonium-2-hydroxypropyl-N,N-dimethylamino methyl carbamoyl methyl cellulose chloride (DQNNED); a mixture of 0.2% (w/v) methylparaben and 0.2% (w/v) DQNNED; and 0.002% (w/v) 3-trimethylammonium-2-hydroxypropyl-N-chitosan (CHI-Q188) were prepared with sterile deionized water. The pH of each solution was adjusted to 7.0±0.2 with 1 M sodium hydroxide. Sterile, deionized water was used as a corntrol. Solutions were stored at room temperature prior to use.

A minimum inhibitory concentration (MIC) test was used to assay antimicrobial activity. The pathogen, *E. coli*, *S. aureus*, or *P. aeruginosa*, was added to a small well containing the polymer solution, phosphate buffer, and nutrient broth, at a concentration of $10^4$ bacterial cells/mL. A range of eight concentrations was usually tested at one time to determine the minimum concentration at which the polymer prevented microbial growth. The concentration of polymer tested ranged from approximately 1600 µg/mL to 2 µg/mL. For each set of tests there was a cell control and a polymer control. The well plates were incubated for 18 to 24 hours at 37° C. A cell in which the polymer concentration effectively inhibited growth appeared clear, while polymer concentrations permitting growth were turbid. The experiments were repeated several times as needed to obtain a good measurement of the average MIC value. Cell wells were judged visually for clarity of the solutions.

A modified preservative efficacy test was used to determine sterilization times (STs) for the test organisms in aqueous samples. The inocula were prepared as described and added to buffered solutions of methylparaben; DQNNED; a mixture of methylparaben and DQNNED; and CHI-Q188 in test tubes. The contents of the test tubes were mixed with a Vortex Genie™ mixer. One hundred µL of the room temperature samples were spread 5 agar plates at time intervals of 0 to 48 hours. The agar plates were then incubated for 18 to 24 hours at 37° C. The agar plates were examined for growth of the test organisms, and the ST was determined to be the time at which test organisms were not recovered from solution. When no endpom was reached in the ST experiments, with bacteria still alive after 48 hours, a minimum possible ST (MPST) was reported instead.

RESULTS

Minimnum Inhibitory Concentrations

The antimicrobial activities of two polymers with quaternary ammonium groups on polysaccharides were compared to methylparaben, a standard cosmetic preservative. See Tables 2 and 3.

MICs for methylparaben were 640 μg/mL for *E. coli*, 800 μg/mL for *P. aeruginosa*, and 1120 μg/ml for *S. aureus*. The MIC for *S. aureus*, a gram positive bacterium, was about two times the MIC for *E. coli*, a gram negative bacterium. The MIC for *P. aeruginosa*, also gram negative, was about 1.25 times the MIC of methylparaben for *E. coli*.

MICs for the polysaccharide DQNNED, which contains a quaternary nitrogen and carbamoyl group, were 480 μg/mL for *E. coli*, 480 μg/mL for *P. aertiginosa*, and 1760 μg/mL for *S. aureus*. This polymer inhibited growth about as well as did methylparaben. The MIC for *S. aureus* was about 3.6 times higher than those for *E. coli* and *P. aeruginosa*.

MICs for a solution containing an equal w/v combination of DQNNED and methylparaben were 320 μg/mL of each compound for *E. coli*, 160 μg/mL of each for *P. aeruginosa*, and 800 μg/mL of each for *S. aureus*. The effect of combining DQNNED and methylparaben on bacterial growth appears to be additive rather than synergistic.

MICs for CHI-Q188 were 16 μg/mL for each of the three bacteria tested, *E. coli, P. aeruginosa*, and *S. aureus*. The CHI-Q188 polymer was about 40 times more effective against *E. coli* than methylparaben, and about 30 times more effective than DQNNED. CHI-Q188 was about 50 times more effective against *P. aeruginosa* than methylparaben, and about 30 times more effective than DQNNED. CHI-Q 188 was about 70 times more effective against *S. aureus* than methylparaben and about 110 times more effective than DQNNED.

TABLE 2

MIC test results for methylparaben and hydroxypropyl trimethylammonium chitosan chloride.

| Compound | Pathogen | Concentration (μg/l) | n[a] |
|---|---|---|---|
| Methylparaben | *E. coli* (25922) | 800 | 2 |
| | | 640[b] | 28 |
| | | 480 | 10 |
| | *S. aureus* (29213) | 1280 | 1 |
| | | 1120[b] | 11 |
| | | 960 | 4 |
| | *P. aeruginosa* (27853) | 800[b] | 12 |
| | | 640 | 11 |
| | | 480 | 8 |
| CHI-Q188 | *E. coli* (25922) | 16[b] | 21 |
| | | 8 | 6 |
| | | 6.4 | 6 |
| | | 4.8 | 1 |
| | *S. aureus* (29213) | 16[b] | 7 |
| | | 8 | 1 |
| | | 6.4 | 3 |
| | | 4.8 | 4 |
| | | 3.2 | 1 |
| | *P. aeruginosa* (27853) | 16[b] | 9 |
| | | 8 | 7 |
| | | 6.4 | 2 |
| | | 4.8 | 1 |

[a]n = the number of times the MIC test gave the particular concentration as the minimum inhibitory concentration
[b]The minimum inhibitory concentration for the compound(s) against a particular pathogen

TABLE 3

MIC test results for methylparaben and DQNNED.

| Compound | Pathogen | Concentration (μg/mL) | n[a] |
|---|---|---|---|
| Methylparaben | *E. coli* (25922) | 800 | 2 |
| | | 640[b] | 28 |
| | | 480 | 10 |
| | *S. aureus* (29213) | 1280 | 1 |
| | | 1120[b] | 11 |
| | | 960 | 4 |
| | *P. aeruginosa* (27853) | 800[b] | 12 |
| | | 640 | 11 |
| | | 480 | 8 |
| DQNNED | *E. coli* (25922) | 640 | 5 |
| | | 480[b] | 14 |
| | | 320 | 1 |
| | *S. aureus* (29213) | 2080 | 4 |
| | | 1920 | 1 |
| | | 1760[b] | 6 |
| | | 1600 | 1 |
| | *P. aeruginosa* (27853) | 480[b] | 12 |
| | | 320 | 4 |
| Methylparaben and DQNNED | *E. coli* (25922) | 320[b] | 16 |
| | *S. aureus* (29213) | 960 | 3 |
| | | 800[b] | 12 |
| | | 640 | 1 |
| | *P. aeruginosa* (27853) | 160[b] | 7 |
| | | 144 | 5 |
| | | 128 | 5 |
| | | 112 | 3 |

[a]n = the number of times the MIC test gave the particular concentration as the minimum inhibitory concentration
[b]The minimum inhibitory concentration for the compound(s) against a particular pathogen Sterilization Times Sterilization times of *E. coli* and *S. aureus* in solutions of methylparabell, DQNNED, and an equal w/v mixture of DQNNED and methylparaben were determined. A 2000 μg/mL methylparaben solution was not rapidly bactericidal; viable test organisms were recovered from this solution after 48 hours. Similar results were obtained for DQNNED alone, and the mixture of DQNNED and methylparaben; again, viable test organisms were recovered from the solutions after 48 hours. See Table 4.

TABLE 4

Sterilization Times of Bacterial Species in Methylparaben, DQNNED, and DQNNED/Methylparaben Mixture.

| Test organism | 0 hr | 1 hr | 2 hr | 4 hr | 24 hr | 48 hr | ST | MPST |
|---|---|---|---|---|---|---|---|---|
| 2000 µg/mL Methylparaben solutions | | | | | | | | |
| E. coli 25922 | + | + | + | + | + | +<br>[12] | – | >48 |
| S. aureus 29213 | + | + | + | + | +<br>[61] | +<br>[28] | – | >48 |
| 2000 µg/mL DQNNED solution | | | | | | | | |
| E. coli 25922 | + | + | + | + | + | + | – | >48 |
| S. aureus 29213 | + | + | + | + | +<br>[84] | + | – | >48 |
| 2000 µg/mL Methylparaben and 2000 µg/mL DQNNED solutions | | | | | | | | |
| E. coli 25922 | + | + | + | + | + | +<br>[24] | – | >48 |
| S. aureus 29213 | + | + | + | + | + | + | – | >48 |
| Sterile, Deionized Water (control) | | | | | | | | |
| E. coli 25922 | + | + | + | + | + | + | – | >48 |
| S. aureus 29213 | + | + | + | + | + | + | – | >48 |

Explanation of symbols in Table 4: +, growth on agar; –, no growth on agar; numbers in brackets (e.g., [12] and [24]) indicate the mean number of colonies growing on agar. ST, sterilization time in hours. MPST, minimum possible sterilization time in hours. All solutions tested contained 3.2 mL of the antimicrobial agent(s) of interest, for a final concentration of 1600 µg/mL of antimicrobial agent; 0.4 mL of 50 mM phosphate buffer, for a final concentration of 5 mM phosphate buffer after dilution; and 0.4 mL of $1 \times 10^5$ bacterial colony forming units ("cfu")/mL, for a concentration of $1 \times 10^4$ cfu/mL after dilution. Tests were performed in triplicate using two different incolua; thus the data represent mean values of six measurements. Aerobic plate counts (APCs) of the inocula were as follows: E. coli 25922, $1.0 \times 10^4$ cfu/mL, and $3.2 \times 10^4$ cfu/mL; S. aureus 29213, $2.2 \times 10^4$ cfu/mL, and $2.0 \times 10^5$ cfu/mL.

Sterilization times for E. coli and S. aureus in solutions of CHI-Q188 are shown in Table 5. The 20 µg/mL CHI-Q188 solution was rapidly bactericidal: test organisms were not recovered at 1.5 hours. Sterilization times were determined as 1.5 hours for E. coli and 30 minutes for S. aureus. See Table 5.

Broad screens will also establish whether compounds in accordance with the present invention also have efficacy against common pathogenic fungi and protozoans.

Future tests will confirm the low toxicity of CHI-Q188 for mammals, first on mammalian cells in vitro, and then in mice, pigs, and other laboratory animals in vivo. Clinical

TABLE 5

Sterilization Times of Bacterial Species in CHI-Q188.

| Test organism | 0 hr | 0.5 | 1 hr | 1.5 | 2 hr | 24 hr | 48 hr | ST | MPST |
|---|---|---|---|---|---|---|---|---|---|
| 20 µg/mL CHI-Q188 solutions | | | | | | | | | |
| E. coli 25922 | + | + | +<br>[10] | –<br>[4] | – | N/A | N/A | 1.5 | – |
| S. aureus 29213 | +<br>[13] | – | – | – | – | N/A | N/A | 0.5 | – |
| Sterile, Deionized Water (control) | | | | | | | | | |
| E. coli 25922 | + | + | + | + | + | + | + | – | >48 |
| S. aureus 29213 | + | + | + | + | + | + | + | – | >48 |

Explanation of symbols in Table 5: +, growth on agar; –, no growth on agar; numbers in brackets (e.g., [10] and [4]) indicate the mean number of colonies growing on agar; ST, sterilization time in hours; MPST, minimum possible sterilization time in hours; N/A, not applicable, as sterilization time was previously reached. All solutions tested contained 3.2 mL of the antimicrobial agents(s) for a final concentration of 16 µg/mL of antimicrobial agent after dilution; 0.4 mL of 50 mM phosphate buffer for a final concentration of 5 mM phosphate buffer after dilution; and 0.4 of $1 \times 10^5$ bacterial cfu/mL for a final concentration of $1 \times 10^4$ colonies/mL after dilution. Tests were performed in triplicate using two different inocula; thus the data represent the mean vlues of six measurements. Aerobic plate counts (APCs) of the inocula were as follows: E. coli 25922, $9.4 \times 10^3$ cfu/mL, and $3.2 \times 10^4$ cfu/mL; S. aureus 29213, $1.3 \times 10^4$ cfu/mL, and $2.2 \times 10^4$ cfu/mL.

trials will then establish safety and efficacy for use in humans, in accordance with pertinent statutes and regulations.

It is also expected that smaller oligomers of CHI-Q188 will exhibit antimicrobial properties. The degree of polymerization (d.p.) in experiments performed to date has been around 100–200. Without wishing to be bound by this theory, it is expected that oligomers with a molecular weight between about 2000 and about 5000, i.e. with a d.p. between about 10 and about 20, may be particularly effective.

It is also expected that the trimethylammonium moiety of CHI-Q188 may be replaced with a dimethylalkyl or dimethylaryl moiety, to yield a 3-(dimethyl-$R^2$-ammonium)-2-hydroxypropyl-N-chitosan, where $R^2$ is a substituted or unsubstituted alkyl or aryl group from $C_2$ to $C_{12}$:

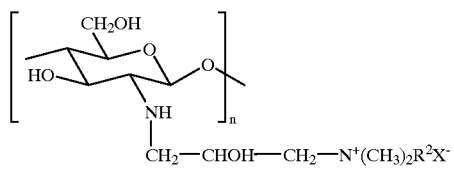

The degree of substitution of the dimethylalkylhydroxypropyl group on the chitosan backbone in the experiments conducted to date has been close to 1.0. It is expected that the degree of substitution may vary from about 0.1 to about 1.0, and produce significant antimicrobial effects. CHI-Q188 with a modified degree of substitution may be represented as:

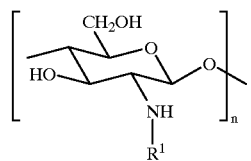

wherein $R^1$ denotes —H, —COCH$_3$ or —CH$_2$—CHOH—CH$_2$—N$^+$(CH$_3$)$_2$R$^2$ X$^-$ in selected proportions corresponding to the degree of substitution; i.e., within a single polymeric or oligomeric molecule, some of the $R^1$s will be —H, some will be —CH$_2$—CHOH—CH$_2$—N$^+$(CH$_3$)$_2$R$^2$ X$^-$, and some may be —COCH$_3$ (optionally), depending on the degree of substitution.

When used as a pharmaceutical, the chitosan derivatives of this invention may be administered to humans or other mammals in pharmaceutical compositions or formulations in combination with one or more pharmaceutically acceptable carriers known in the art. The compounds may also be administered as pharmaceutically acceptable salts. Suitable pharmaceutical adjuvants for injection solutions include stabilizing agents, sollubilizing agents, buffers, and viscosity regulators. These injectable solutions may be injected intramuscularly, intraperitoneally, or intravenously. Because the compounds of this invention are resistant to digestion, oral administration is preferred in situations where oral administration is practical. Suitable pharmaceutical adjuvants for oral administration include stabilizing agents, solubilizing agents, buffers, fillers, flavorants, and coatings. The compounds may also be administered topically. Suitable adjuvants for topical application include stabilizing agents and solubilizing agents. Sutures and bandages may be coated with CHI-Q188 blended with other materials.

The novel chitosan derivatives of this invention may be incorporated into detergent mixtures to impart antimicrobial characteristics to the detergents.

The chitosan derivatives may also be blended with film-forming polymers to make films with antimicrobial properties. Examples of such film-forming polymers are well-known in the art, and include for example polyvinyl alcohol, ethylene-vinyl alcohol copolymer, and ethylene-acrylic acid copolymer.

In the specification and claims, a concentration or amount of a compound or composition is considered to be "effective" if it reduces the level of bacterial growth or infection to a statistically significant degree.

The complete disclosures of all references cited in this specification are hereby incorporated by reference. In the event of an otherwise irreconcilable conflict, however, the present specification shall control.

We claim:

1. A process for killing bacteria, comprising administering to the bacteria an effective amount of the compound

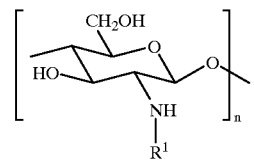

wherein $R^1$ denotes —H, —COCH$_3$, or —CH$_2$—CHOH—CH$_2$—N$^+$(CH$_3$)$_2$R$^2$X$^-$, wherein the proportion of $R^1$s that are —CH$_2$—CHOH—CH$_2$—N$^+$(CH$_3$)$_2$R$^2$X$^-$ is between about 10% and 100%; wherein $R^2$ denotes a substituted or unsubstituted alkyl or aryl group from $C_1$ to $C_2$; wherein X$^-$ denotes an anion; and wherein the degree of polymerization n is 5 or greater.

2. A process as recited in claim 1, wherein the bacteria are killed in a cosmetic preparation.

3. A process as recited in claim 1, wherein the bacteria are killed in a mammalian host.

4. A method as recited in claim 1, wherein the bacteria are killed in a detergent preparation.

5. A method as recited in claim 1, wherein the bacteria are killed in a blend of an effective amount of the recited compound and a film-forming polymer.

6. A method as recited in claim 5, wherein the film-forming polymer is selected from the group consisting of polyvinyl alcohol, ethylene-vinyl alcohol copolymer, and ethylene-acrylic acid copolymer.

* * * * *